US011553849B2

(12) United States Patent
Schmalenberg et al.

(10) Patent No.: US 11,553,849 B2
(45) Date of Patent: Jan. 17, 2023

(54) MICROPHONE WITH STRUCTURAL MATCHED FILTER FOR HEART RATE MEASUREMENT

(71) Applicant: Toyota Motor Engineering & Manufacturing North America, Inc., Plano, TX (US)

(72) Inventors: Paul D. Schmalenberg, Ann Arbor, MI (US); Ercan Mehmet Dede, Ann Arbor, MI (US); Frederico Marcolino Quintao Severgnini, Ann Arbor, MI (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 5 days.

(21) Appl. No.: 17/233,985

(22) Filed: Apr. 19, 2021

(65) Prior Publication Data

US 2022/0330836 A1    Oct. 20, 2022

(51) Int. Cl.
*A61B 5/024* (2006.01)
*B60W 40/08* (2012.01)
*A61B 5/00* (2006.01)

(52) U.S. Cl.
CPC .......... *A61B 5/024* (2013.01); *A61B 5/6893* (2013.01); *B60W 40/08* (2013.01); *B60W 2040/0872* (2013.01)

(58) Field of Classification Search
None
See application file for complete search history.

(56) References Cited

U.S. PATENT DOCUMENTS

| 5,853,005 A | 12/1998 | Scanlon |
| 6,809,643 B1 | 10/2004 | Elrod et al. |
| 2013/0030256 A1* | 1/2013 | Fujita ................. A61B 7/00 600/300 |
| 2016/0074260 A1 | 3/2016 | Belsinger, Jr. et al. |

FOREIGN PATENT DOCUMENTS

| DE | 102016003312 A1 | 10/2016 |
| FR | 2980354 A1 | 3/2013 |

OTHER PUBLICATIONS

Qian et al., "Acousticcardiogram: Monitoring Heartbeats Using Acoustic Signals on Smart Devices," URL: https://www.researchgate.net/Publication/328379120_Accousticcardiogram_Monitoring_Heartbeats_Using_Acoustic_Signals_on_Smart_Devices, Apr. 2018.

* cited by examiner

*Primary Examiner* — Thomas S McCormack
(74) *Attorney, Agent, or Firm* — Dinsmore & Shohl LLP (57) ABSTRACT

A system for acoustically monitoring a heartbeat includes an acoustic body having a first material in contact with a second material, a density and a propagation speed of sound of the first material is matched with a density and a propagation speed of sound of a human body, and a density and a propagation speed of sound of the second material is matched with the density and the propagation speed of sound of the first material, a covering material in contact with a first surface of the acoustic body formed by the first material, and a microphone acoustically coupled to a second surface of the acoustic body formed by the second material.

20 Claims, 7 Drawing Sheets

MICROPHONE WITH STRUCTURAL MATCHED FILTER FOR HEART RATE MEASUREMENT

TECHNICAL FIELD

The present specification generally relates to devices for acoustically monitoring a heartbeat through a seat and transferring the heartbeat sound to a microphone located remotely from the body.

BACKGROUND

Detecting a heartbeat of an occupant of a seat, such as a vehicle seat, currently requires placing a microphone on the seat surface of the seat. However, the microphone is a rigid structure that reduces the comfort of the occupant. These current techniques are necessary because non-contact monitoring of a heartbeat is very difficult and inefficient when an air gap between the body and the microphone is present because sound pressure from the heart beating within the body is mostly reflected back into the body because of poor acoustic coupling between the human body and the air.

Accordingly, a need exists for improved monitoring a heartbeat through a seat and transferring the heartbeat sound to a microphone located remotely from the body.

SUMMARY

In one embodiment, a system for acoustically monitoring a heartbeat includes an acoustic body having a first material in contact with a second material, a density and a propagation speed of sound of the first material is matched with a density and a propagation speed of sound of a human body, and a density and a propagation speed of sound of the second material is matched with the density and the propagation speed of sound of the first material, a covering material in contact with a first surface of the acoustic body formed by the first material, and a microphone acoustically coupled to a second surface of the acoustic body formed by the second material.

In another embodiment, a system for acoustically monitoring a heartbeat includes an acoustic body having a first material in contact with a second material, a density and a propagation speed of sound of the first material is matched with a density and a propagation speed of sound of a human body, and a density and a propagation speed of sound of the second material is matched with the density and the propagation speed of sound of the first material, a covering material in contact with a first surface of the acoustic body, a dome shaped material coupled to a second surface of the acoustic body, the dome shaped material has an acoustic impedance that is greater or less than the acoustic impedance of the second material, and a microphone is positioned within the second material of the acoustic body and an acoustic sensitive element of the microphone is directionally positioned toward the dome shaped material.

In another embodiment, a vehicle seat for a vehicle includes a first material in contact with a second material forming an acoustic body, wherein the acoustic body is positioned within the vehicle seat, a covering material of the vehicle seat in contact with a first surface of the acoustic body, and a microphone acoustically coupled to a second surface of the acoustic body, wherein a density and a propagation speed of sound of the first material is matched with a density and a propagation speed of sound of a human body, and a density and a propagation speed of sound of the second material is matched with the density and the propagation speed of sound of the first material.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

The embodiments disclosed herein include devices for acoustically monitoring a heartbeat through a seat, such as a vehicle seat, and transferring the heartbeat sound to a microphone located remotely from the body. More specifically, embodiments depicted and described in the present application provide various acoustic body configurations that reduce the transmission loss from the source of an acoustic signal, for example, generated by a heartbeat, to a remotely located microphone. Remote monitoring of acoustic signals such as a heartbeat of an individual in a vehicle enables systems such as driver monitoring and awareness systems to be implemented without direct contact of a heart-sensing device to the driver.

Current acoustic heart monitors generally make direct contact with the skin. These use miniaturized microphones that are mounted on a metal plate. The other side of the metal plate makes contact directly with the skin, similar to a stethoscope. However, the challenge of using such a system in a seat is that there is not a readily available or comfortable approach for directly monitoring a heartbeat. That is, these approaches necessitate the implementation of hard surfaces on the seat to get good body contact so that an acoustic signal can be transferred generated by the heart to the microphone. To improve the comfort to a user being whose heart is being monitored and achieve remote monitoring, embodiments of the present disclosure utilize an acoustic body to efficiently transfer the heartbeat sound to a microphone located remote from the body.

Embodiments of devices for acoustically monitoring a heartbeat through a seat, such as a vehicle seat, and transferring the heartbeat sound to a microphone located remotely from the body disclosed herein are described in the context of a vehicle seat and driver of the vehicle. However, it should be understood that the device may be implemented in various applications such as patient monitoring within a hospital bed, nursing home or personal health heart monitoring through furniture such as couches, beds, chairs or the like.

As will be described in detail herein, some techniques also focus and enhance the heartbeat sound directed to the microphone location while rejecting unwanted frequencies by a physical filter to improve signal-to-noise ratio (SNR) at the microphone, before signal processing begins.

Embodiments described herein includes a device that removes the air gap so that a microphone configured to capture acoustic sounds resulting from a heart beating may be achieved in a non-contact way. That is, non-contact monitoring of a heartbeat enables heartbeat monitoring systems to be implemented, for example, within a vehicle seat to monitor the heartbeat of a driver. In some embodiments, a first side of the device attaches to the seat covering material and to a second side of the device includes a microphone. The device includes a transfer material that transfers the heartbeat sound to the microphone by minimizing or eliminating transmission through the air.

The various systems and devices methods for monitoring a heart rate acoustically and transferring the heartbeat sound to a microphone slightly remote from the body will now be described in more detail herein with specific reference to the corresponding drawings as example but not limiting embodiments.

Figure 1:
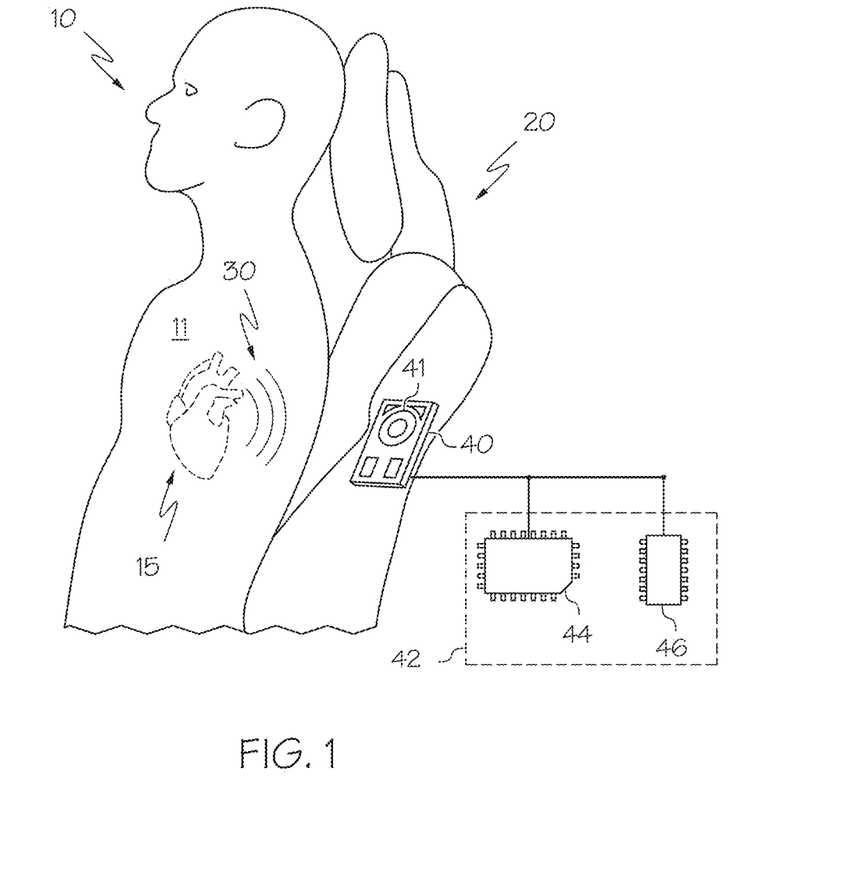
FIG. 1 schematically depicts a passenger seated in a seat configured to transfer the heartbeat sound of the passenger to a microphone located remotely from the body of the passenger according to one or more embodiments shown and described herein.

Turning now to the drawings wherein like numbers refer to like structures, and particularly to FIG. 1, a subject 10 seated in a seat, such as a seat, such as a vehicle seat, 20 configured to transfer the heartbeat sound 30 from the body 11 of the subject 10 to a microphone 40 located remotely from the body 11 of the subject 10. A seat's surface (e.g., a seat covering material) is generally pliable and forms to the body's contours to enable comfort. Accordingly, there is a further need to provide a system 1 that conforms to a contour of a seat and is pliable such that it can conform to the body's contours to enable comfort.

As used herein, the microphone 40 may be any device capable of converting pressure variations of a sound wave to an electrical signal that may be transmitted to and/or captured by an electronic control unit 42 comprising a processor 44 and a non-transitory computer readable memory 46. The electronic control unit 42 is communicatively coupled to the microphone 40 and optionally other components of the system 1. The microphone 40 includes an acoustic sensitive element 41 which may also be referred to as the sensitive transducer element. For example, the acoustic sensitive element 41 converts sound waves incident thereon to mechanical motion by mean of a diaphragm and then the motion is converted to an electrical signal.

The electronic control unit 42 may be any device or combination of components comprising a processor 44 and non-transitory computer readable memory 46. The processor 44 may be any device capable of executing the machine-readable instruction set stored in the non-transitory computer readable memory 46. Accordingly, the processor 44 may be an electric controller, an integrated circuit, a microchip, a computer, or any other computing device. The non-transitory computer readable memory 46 is coupled to the processor 44. The non-transitory computer readable memory 46 may comprise RAM, ROM, flash memories, hard drives, or any non-transitory memory device capable of storing machine-readable instructions such that the machine-readable instructions can be accessed and executed by the processor 44. The machine-readable instruction set may comprise logic or algorithm(s) written in any programming language of any generation (e.g., 1GL, 2GL, 3GL, 4GL, or 5GL) such as, for example, machine language that may be directly executed by the processor 44, or assembly language, object-oriented programming (OOP), scripting languages, microcode, etc., that may be compiled or assembled into machine readable instructions and stored in the non-transitory computer readable memory 46. Alternatively, the machine-readable instruction set may be written in a hardware description language (HDL), such as logic implemented via either a field-programmable gate array (FPGA) configuration or an application-specific integrated circuit (ASIC), or their equivalents. The electronic control unit 42 may configured to receive signals from the microphone 40 whereby the electrical signals may be processed, filtered, amplified, and the like to identify a desired waveform such as a waveform of a heartbeat. The waveform of the heartbeat may be analyzed to determine heartrate, rhythm, and the like for use by a system such a driver health or awareness system.

Figure 2:
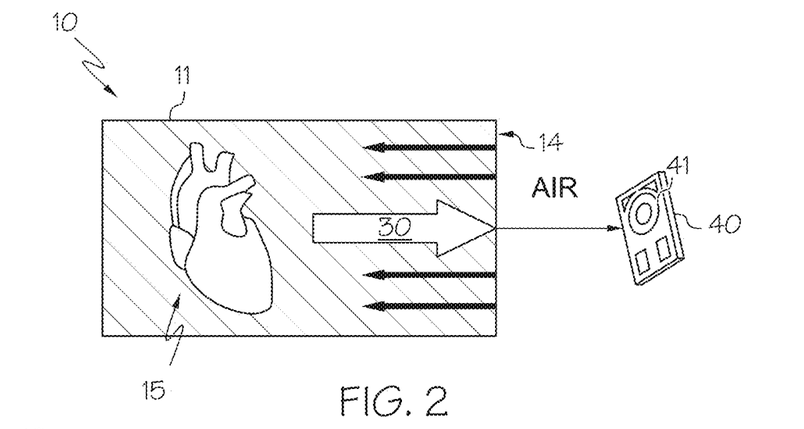
FIG. 2 schematically depicts an air gapped heartbeat monitoring configuration.

Referring to FIG. 2, an air gapped heartbeat monitoring configuration is depicted and described herein. The instant configuration is provided to present the challenges associated with remote sensing of a heartbeat in order to provide a greater understanding of the embodiments described herein and the technical advantages that an acoustic body provide to the remotely monitoring and measuring a heartbeat. A non-contact, remote sensing configuration for detecting a heartbeat includes positioning a microphone 40 away from the body 11 of the subject 10 heart 15 that is to be sensed. More particularly, that includes having an air gap between the sensor, for example a microphone 40 and the skin 14 of the subject 10.

Acoustically, this is difficult since sound transmission from the body's interior to air surrounding it is very inefficient. Most of the sound generated by the heart and cardiovascular system is reflected back into the body 11 where it ultimately is absorbed by non-rigid parts of the body. Only about 0.06% of the sound pressure from the heartbeat exits the body to the air as illustrated by the size of the arrows illustrated in FIG. 2. For example, such a configuration may result in a −15 dB or more transmission loss between the body 11 and the microphone 40.

In this case, a microphone 40 positioned in the air has difficulty in receiving the sound 30 of the heartbeat. The difficulty is amplified in noisy environments. The difficulty arises because very little pressure from the sound waves generated within the body 11 transfers to the air. That is, the body 11, which has a similar sound impedance to water, is denser than air, so it takes more energy to generate a sound wave therein, but once a wave has started, it will travel faster than it does in air. When sound waves encounter a change in the density of the material, depending on the difference in density and propagation speed of sound (e.g., the acoustic impedance) in the adjacent material, a portion of the sound wave will be transferred to the adjacent material, while the other portion will be reflected back. The relationship between the density (d, in kg/m$^3$) and the propagation speed of sound (c, in m/s) for a material is referred to as the acoustic impedance (Z). In general, acoustic impedance (Z) equals the product of the density (d) and propagation speed of sound (c) for a particular material. That is, if the density (d) of a tissue increases, impedance (Z) increases. Similarly, if the speed of sound (c) increases, then impedance (Z) also increases. The ability of a sound wave to transfer from one material type to another depends on the difference in impedance of the two materials. The amount of reflection that occurs in a perpendicular direction can be expressed by the term reflection fraction=$[(Z_2-Z_1)/(Z_2+Z_1)]^2$, where $Z_1$ is the acoustic impedance of the first material and $Z_2$ is the acoustic impedance of the second material. That is, the resulting reflection fraction refers to the percentage of sound reflected by the second material.

In the case of a body 11 to air system, a large amount of the sound wave is reflected back into the body 11. As a result, a low amount of the energy of the sound wave exits and travels through the air. Accordingly, on a small amount of energy representing the heartbeat sound 30 is detectable by the microphone 40. This small amount of energy is typically insufficient to determine a heartbeat signal.

Accordingly, the present disclosure presents new systems for efficiently transferring the sound 30 of a heartbeat from the body 11 of a subject 10 to a microphone 40 such that the transmission loss may be significantly reduced. Moreover, the systems disclosed herein provide acoustic body configurations for transferring the sound 30 of a heartbeat from the body 11 of a subject 10 to a microphone 40 that are pliable and capable of forming to the contours of a body 11. The capability of the acoustic body to be pliable and capable of forming to the contours of a body 11 further enables the system 1 to be implemented in objects such as chairs, vehicle seats, beds, wheel chairs, and the like which have a surface that are in direct contact with the clothing and/or body 11 of a subject 10. The pliability enables the system 1 to be comfortably applied as opposed to needing rigid surfaces that do not provide the same levels of comfort.

Figure 3A:
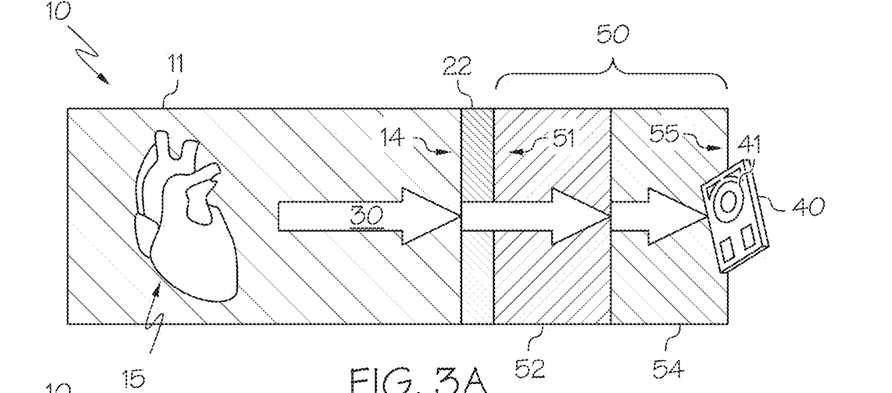
FIG. 3A schematically depicts an illustrative example of a heartbeat sound monitoring system having a microphone located remotely from the body, according to one or more embodiments shown and described herein.
Figure 3B:
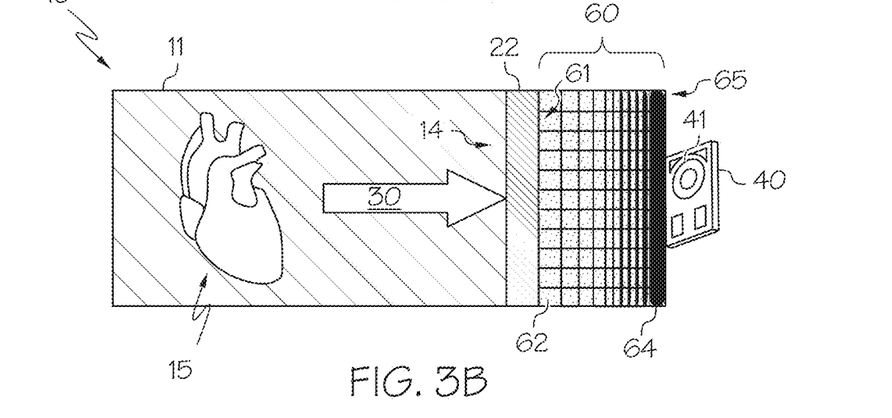
FIG. 3B schematically depicts another illustrative example of a heartbeat sound monitoring system having a microphone located remotely from the body, according to one or more embodiments shown and described herein.

Referring not to FIGS. 3A and 3B, illustrative examples of a heartbeat sound 30 monitoring system 1 having a microphone 40 located remotely from the body 11 of a subject 10 are depicted. In general, the system 1 implements an acoustic body (50, FIG. 3A and 60, FIG. 3B) that have specified density and propagation speed of sound characteristics that enable a −5 db or less transmission loss in the transmission of the acoustic signal, for example of a heartbeat, from the body 11 to the microphone 40. In each of the illustrative examples depicted in FIGS. 3A and 3B, the acoustic sensitive element 41 is directionally positioned toward the first surface 51 and 61 of the acoustic body 50 and 60 and the seat covering material 22. By varying the density and propagation speed of sound of the materials of the acoustic body (50, FIG. 3A and 60, FIG. 3B) a heartbeat sound 30 may be efficiently transferred to a remotely positioned microphone 40 while enabling the system 1 to be closely integrated within objects such as a seat, such as a vehicle seat, 20 contacting the body 11 of the subject 10.

In FIG. 3A, an acoustic body 50 having a layered configuration is depicted. The acoustic body 50 includes a first material 52 and a second material 54 positioned adjacent and in contact with each other. The acoustic body 50 includes a first surface 51 (e.g., the first surface 51 is formed by the first material 52) and a second surface 55 (e.g., the second surface 55 is formed by the second material 54). The first surface 51 is positioned in contact with, for example, a seat covering material 22 of a seat, such as a vehicle seat, 20. The second surface 55 is positioned in contact with the microphone 40 or a microphone mount or housing, which may be a rigid material for affixing the microphone 40 to the acoustic body 50. Moreover, the acoustic body 50 and microphone 40 may be positioned and sized to fit within the structure of the seat 20. In this way, the system 1 can be installed into the seat's internals without compromising look and feel of the seat 20.

A seat covering material 22 of the seat 20 is generally pliable and forms to the body's contours to enable comfort. This is achieved by selecting materials that are pliable and/or formable that also has a density and propagation speed of sound property that enables low loss transfer of sound there through.

The first material 52 is a material that has a density and propagation speed sound property which is equal to, a little more than, or a little less than the density and propagation speed of sound of the body 11. That is, the density and propagation speed of sound of the first material 52 and the body 11 should be closely matched. As used herein, the term "matched" refers to acoustic impedance relationships between adjacent materials having a reflection fraction of about 50%, 45%, 40%, 35%, 30%, 25%, 20%, 15%, 10%, 5%, 4%, 3%, 2%, 1% or less. The term "matched" does not necessarily mean equal. The term "matched" may refer to a close relationship between the acoustic impedances of adjacent materials. The average propagation speed for sound in the body 11 (e.g., body tissue) is about 1540 m/s. The density of a body 11 can be approximated as 1100 kg/m$^3$, however, overall body density varies depending on the composition of the body. Therefore, the density and propagation speed of sound for the first material 52 may be equal to or a little more than the average propagation speed for sound in the body 11 and density of the body 11. For example, but without limitation, the density of the first material 52 may be between 1200 kg/m$^3$ and 1700 kg/m$^3$. Additionally, the propagation speed of sound of the first material 52 may be about 1500 m/s to about 2000 m/s or any value therebetween. The density and propagation speed of sound for the first material 52 should be relatively close to that of the body 11 so an efficient propagation of sound form the body to the first material 52 can be achieved. For example, the first material 52 may be a liquid, gel, semi viscous, or other pliable material. In some embodiments, the first material 52 may be glycerol, which has a density of about 1260 kg/m$^3$ and a propagation speed of sound of 1850 m/s. The first material 52 may be mixed with other substances to achieve a more or less viscous material. It is appreciated that any expressed ranges includes both the boundary values, unless otherwise specified.

The second material 54 is a material that has a density and propagation speed sound which more closely matches the density and propagation speed sound of the microphone 40 or microphone mounting structure. However, the density and propagation speed sound of the second material 54 is not significantly larger than the density and propagation speed sound of the first material 52. For example, but without limitation, the density of the second material 54 may be between 1500 kg/m$^3$ and 2500 kg/m$^3$. Additionally, the propagation speed of sound of the second material 54 may be about 1800 m/s to about 3000 m/s or any value therebetween. That is, the density and propagation speed of sound of the first material 52 and the second material 54 should be matched. As defined above, the term "matched" refers to acoustic impedance relationships between adjacent materials having a reflection fraction of about 50%, 45%, 40%, 35%, 30%, 25%, 20%, 15%, 10%, 5%, 4%, 3%, 2%, 1% or less. These properties generally include solids such as polymers and resins like a nylon infused plastic and some metals. In some embodiments, the second material 54 may be a solid. Embodiments of the acoustic body 50 are not limited to only a first and second material 52 and 54. The acoustic body 50 may include two or more materials each having a greater density and/or propagation speed of sound as function of the distance from the body 11.

It should be understood that the acoustic body 50 is not limited to a layered or adjacently oriented configuration of materials. Furthermore, in some embodiments, the first material 52 and/or the second material 54 may be an acoustic metamaterial as described in more detail herein. In yet some embodiments, an acoustic metamaterial may be included within the acoustic body 50 with one or more other materials.

Referring now to FIG. 3B, in some embodiments, the illustrated acoustic body 60, which may functionally operate the same or similar to the acoustic body 50 as shown and described in FIG. 3A, may also comprise a first material 62 and a second material 64 in contact with each other. Similar to the acoustic body 50 depicted in FIG. 3A, the acoustic body 60 includes a first surface 61 and a second surface 65. The first surface 61 is positioned in contact with, for example, a seat covering material 22 of a seat, such as a vehicle seat, 20. The second surface 65 is positioned in contact with the microphone 40 or a microphone mount or housing, which may be a rigid material for affixing the microphone 40 to the acoustic body 60.

In some embodiments, the second material 64 may be a matrix material and the first material 62 may be a liquid or gel that is disposed within the matrix material and thereby in contact. The second material 64 may be a matrix material having a porosity that decreases as a function of distance from the body. In other words, the second material 64 may be a matrix material that increases in fill factor closer the acoustic body 60 is to the microphone 40. A matrix material having a gradient in fill factor from the first surface 61 to the second surface 65 of the acoustic body 60. That is the amount of the first material 62 decreases as the amount of the second material 64 increases within the acoustic body 60 as the distance from the first surface 61 of the acoustic body 60 increases.

The first material 62 is a material that has a density and propagation speed sound property which is equal to, a little more than, or a little less than the density and propagation speed of sound of the body 11. The density and propagation speed of sound for the first material 62 may be equal to or a little more than the average propagation speed for sound in the body 11 and density of the body 11. For example, but without limitation, the density of the first material 62 may be between 1200 kg/m$^3$ and 1700 kg/m$^3$. Additionally, the propagation speed of sound of the first material 62 may be about 1500 m/s to about 2000 m/s or any value therebetween. The density and propagation speed of sound for the first material 62 should be relatively close to that of the body 11 so an efficient propagation of sound form the body 11 to the first material 62 can be achieved. For example, the first material 62 may be a liquid, gel, semi viscous, or other pliable material. Additionally, for example, but without limitation, the density of the second material 64 may be between 1500 kg/m$^3$ and 2500 kg/m$^3$. Additionally, the propagation speed of sound of the second material 64 may be about 1800 m/s to about 3000 m/s or any value therebetween.

Figure 4:
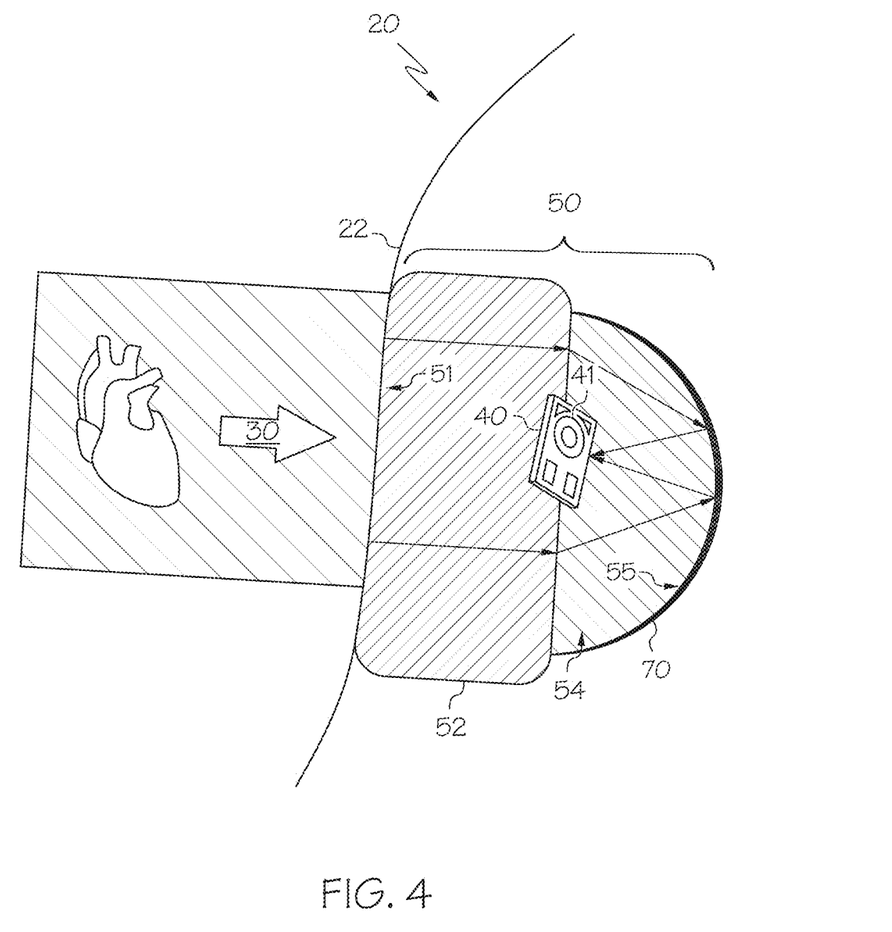
FIG. 4 schematically depicts an illustrative example of a heartbeat sound monitoring system having a microphone located remotely from the body utilizing a dome shaped reflection surface, according to one or more embodiments shown and described herein.

Turning now to FIG. 4, illustrative example of a heartbeat sound monitoring system 1 having a microphone 40 located remotely from the body that utilizes a dome shaped reflection surface 70 is depicted. FIGS. 3A and 3B depict how different configurations of material within the acoustic body 50 and 60 improve the propagation of a heartbeat sound from the body to a remotely positioned microphone 40. FIG. 4 now depicts an example configuration that improves the propagation of a heartbeat sound 30 from the body 11 to a remotely positioned microphone 40 by applying the configurations of materials within the acoustic body 50 and 60 described with reference to FIGS. 3A and 3B, and by structuring the shape of the acoustic body 50 and the position of the microphone 40 to enhance reception of the heartbeat sound 30 by the microphone 40.

As discussed in more detail herein, an angle of incidence, $\phi$, of a plane wave, for example the heartbeat sound 30, on the microphone 40 impacts the transmission loss. That is, higher angles of incidence $\phi$ generally result in higher transmission losses. As used herein, angles of incidence $\phi$ are measured from a normal to the surface of a material boundary and the microphone 40. In the present embodiment, FIG. 4 depicts an acoustic body 50 that further includes a dome shaped reflection surface 70 positioned over the second surface 55 of the acoustic body 50. The dome shaped reflection surface 70 comprises a dense material, for example, a material denser than the second material 54. In some embodiments, the dome shaped reflection surface 70 is formed of a metallic material. A concave portion of the dome shaped reflection surface 70 is positioned on the second surface 55 facing the first surface 51 of the acoustic body 50, which further faces the source of the sound to be captured by the microphone 40, such as the heart 15.

Additionally, in the present embodiment, the microphone 40 may be at least partially positioned within at least a portion of the second material 54. Furthermore, the acoustic sensitive element 41 is directionally positioned toward dome shaped reflection surface 70. Accordingly, as the heartbeat sound 30 propagates from the body 11 and through the first material 52 and second material 54, it impinges and reflects off the dome shaped reflection surface 70 as indicated by the illustrated arrows. Subsequently, as further illustrated by the arrows, the reflected sound is directed by the shape of the dome shaped reflection surface 70 toward the acoustic sensitive element 41 of the microphone 40. A configuration that implements the dome shaped reflection surface 70 is used to focus the sound pressure toward the microphone interface. As a non-limiting example, the dome shaped reflection surface 70 may be used in the seat 20 where the position of the source of the sound (e.g., the position of the heart 15) may vary between subjects. For example, for a short driver the location of the heart may be lower on the seat back than a taller driver. Implementation of the dome shaped reflection surface 70 may allow for a broader range of origination positions of the heartbeat sound 30 to be focused on a single microphone 40 thereby potentially reducing the need to multiple acoustic bodies and microphone systems to be implemented throughout the interior of the seat, such as a vehicle seat, 20.

Figure 5:
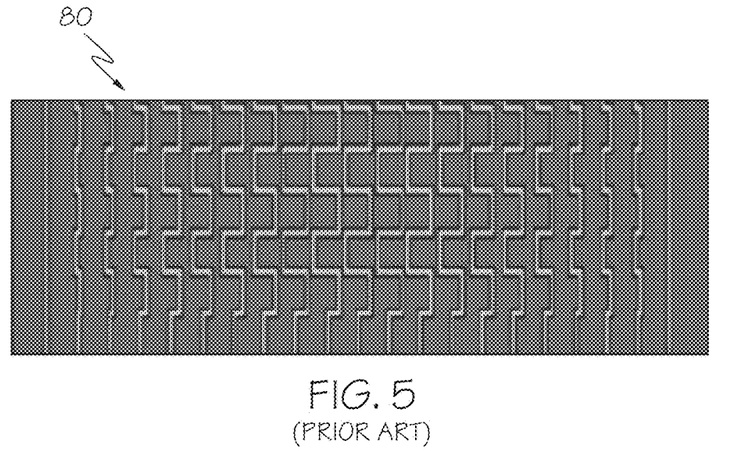
FIG. 5 depicts an illustrative example cross-section view of a metamaterial, according to one or more embodiments shown and described herein.

Some embodiments may also utilize metamaterial structures to improve the focusing and/or filtering of the sound for capture by the microphone 40. FIG. 5 depicts an illustrative cross-section view of an example metamaterial 80 proposed by Jandali et al. in "High transmission acoustic focusing by impedance-matched acoustic meta-surfaces", Appl. Phys. Lett. 108, 031902 (2016). Acoustic metamaterials control, direct, and manipulate sound in the form of sonic, infrasonic, or ultrasonic waves in gases, liquids, and solids. Metamaterials can be textured with nanoscale wrinkles to control sound signals, such as filter out unwanted frequencies or focusing a signal. The materials can be made through a high-precision, multi-layer deposition process. The thickness of each layer can be controlled within a fraction of a wavelength. The material is then compressed, creating precise wrinkles whose spacing can cause scattering of selected frequencies.

Figure 6:
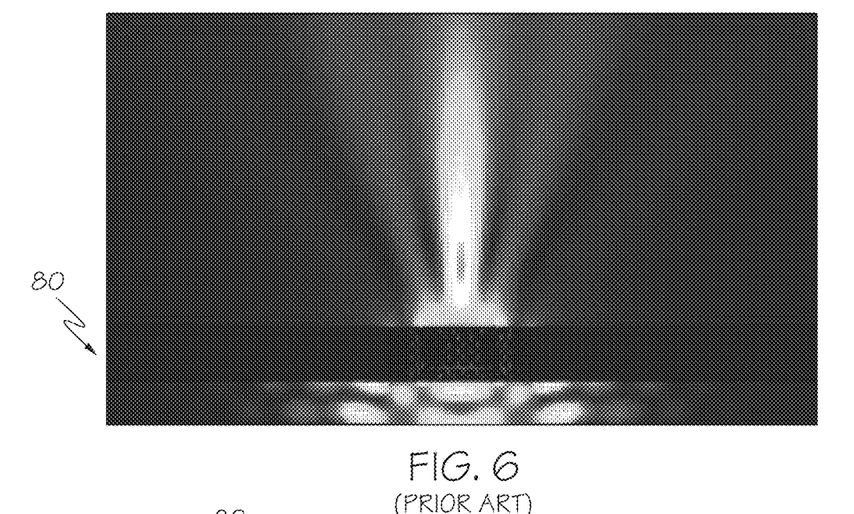
FIG. 6 depicts a simulation of focusing acoustic waves with a metamaterial, according to one or more embodiments shown and described herein.
Figure 7:
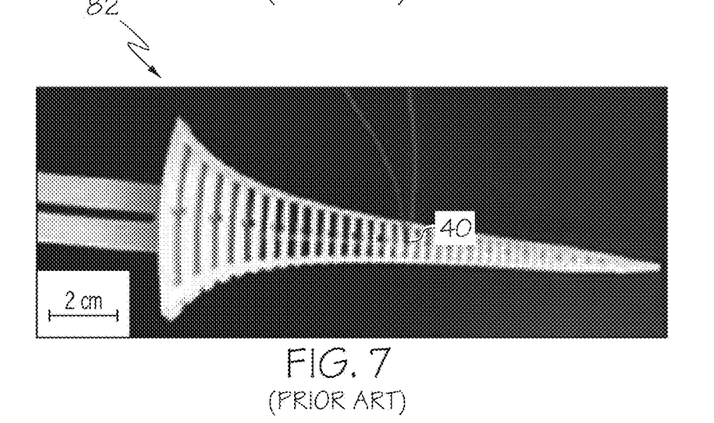
FIG. 7 depicts an illustrative example of an acoustic metamaterial filter, according to one or more embodiments shown and described herein.

With respect to embodiments for monitoring a heartbeat, the frequencies of interest are around 20 to 150 Hz. Metamaterial structures can be utilized as their structure can be many times smaller than the wavelength of the sound. As discussed above, the inclusion of metamaterial structures within the acoustic body and microphone 40 enables focusing of the acoustic wave and filtering unnecessary frequencies, which block out unwanted noise. FIG. 6 depicts an illustrative example of the metamaterial 80 receiving an unfocused acoustic signal on the lower portion of the simulation and the resulting focused pressure field above the metamaterial 80. Additionally, with reference to FIG. 7, an example acoustic metamaterial filter 82 proposed by Xinjing et al. in "An Acoustic Metamaterial-Based Sensor Capable of Multiband Filtering and Amplification," IEEE Sensors Journal, vol. 20, no. 8, pp. 4413-4419, 15 Apr. 15, 2020 is depicted. The microphone 40 is positioned at a predefined location along the length acoustic metamaterial filter 82 such that as an acoustic wave propagates along the acoustic metamaterial filter 82 from the tip to the wide end, on the selected frequencies that correspond to the gap that the microphone 40 is located in are captured by the microphone 40. In that way, the acoustic metamaterial filter 82 can be used to selectively filter out frequency ranges that are not of interest to the implementation. For example, the acoustic metamaterial filter 82 may be implemented as part of the acoustic body of the present disclosure so that frequencies higher than 150 Hz may be filtered out thereby improving the detection of predefined sounds such as a heartbeat. It is understood that focusing and/or filtering of acoustic signals can be accomplished using metamaterials within the systems described herein.

Figure 8A:
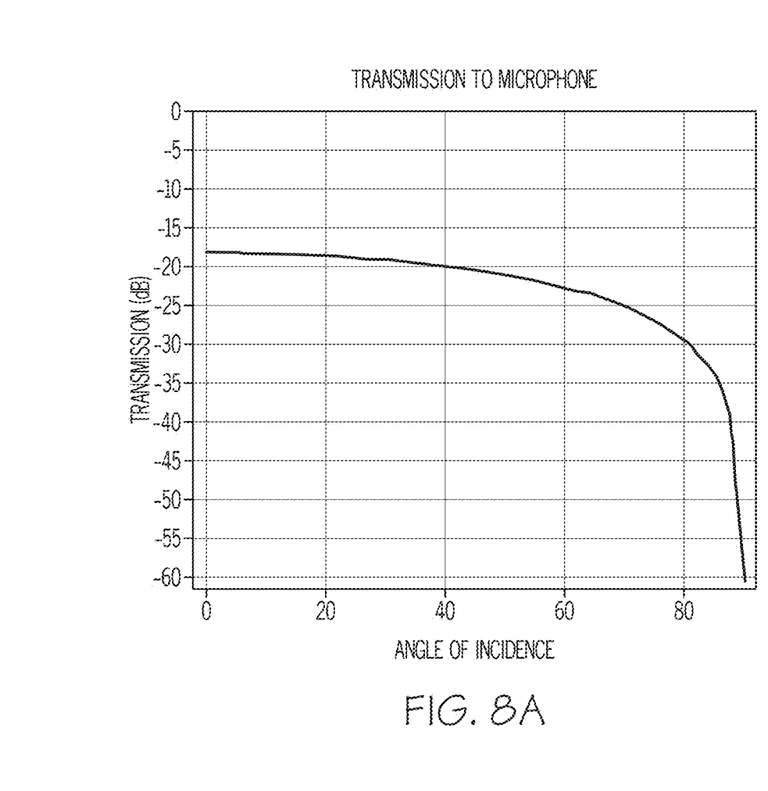
FIG. 8A depicts a chart showing the relationship between transmission loss and the angle of incidence of a plane wave in the air gapped heart beat monitoring configuration depicted in FIG. 8B.
Figure 8B:
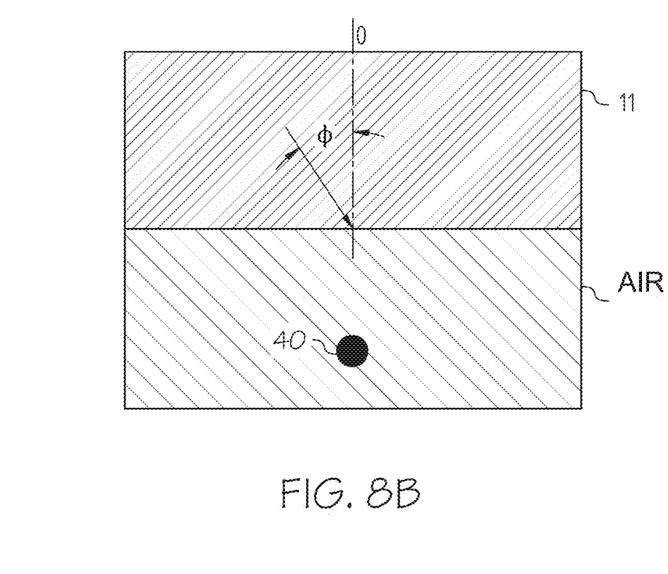
FIG. 8B depicts an air gapped heart beat monitoring configuration.
Figure 9A:
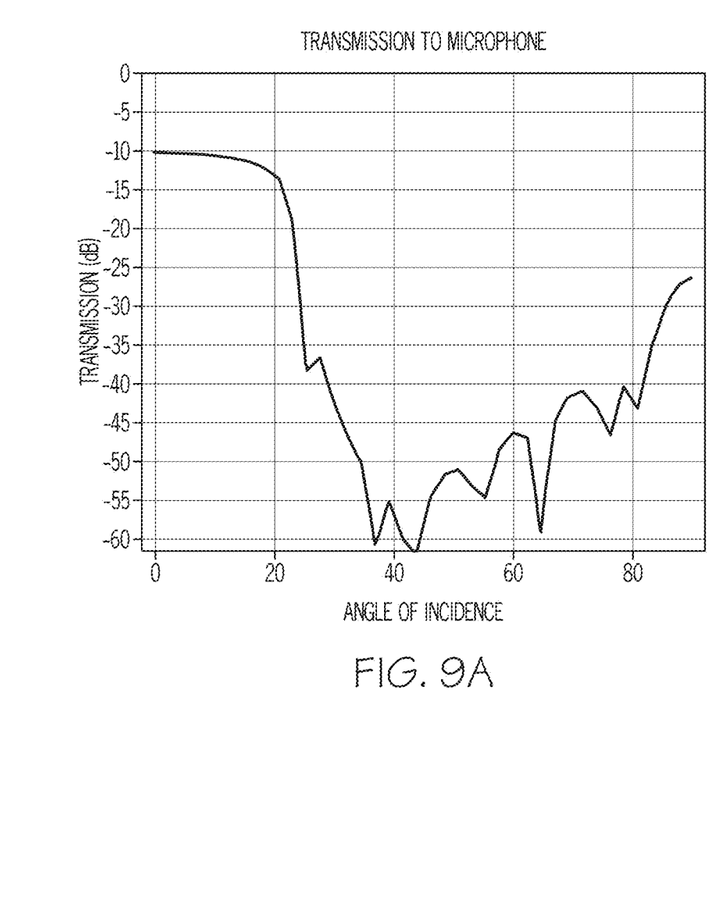
FIG. 9A depicts a chart showing the relationship between transmission loss and the angle of incidence of a plane wave in a body-to-metal plate heartbeat monitoring configuration depicted in FIG. 9B.
Figure 9B:
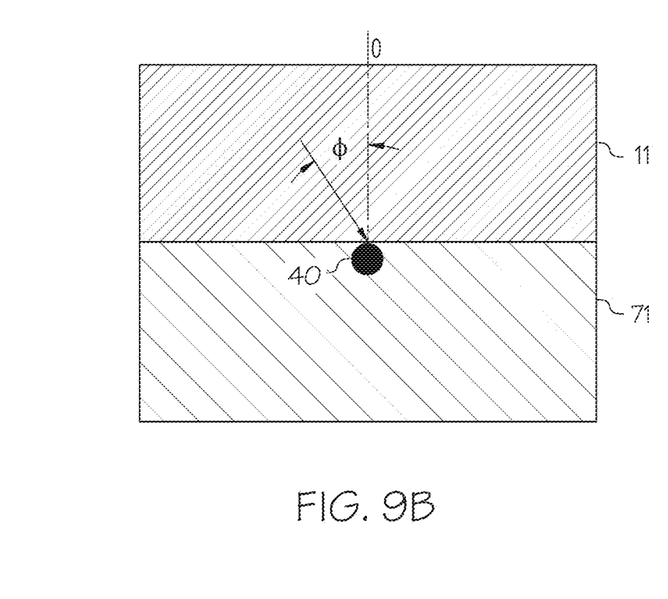
FIG. 9B depicts an body-to-metal plate heartbeat monitoring configuration.
Figure 10A:
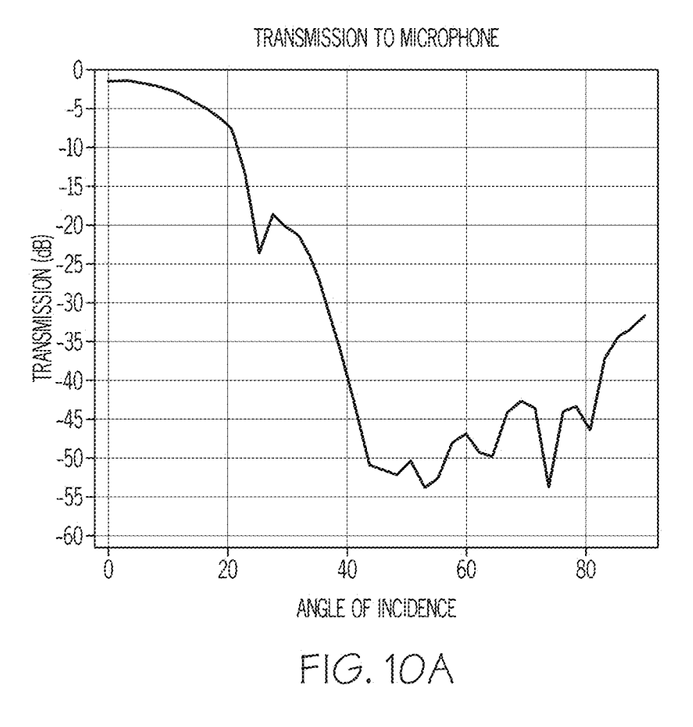
FIG. 10A depicts a chart showing the relationship between transmission loss and the angle of incidence of a plane wave in an acoustic body heartbeat monitoring configuration depicted in FIG. 10B, according to one or more embodiments shown and described herein.
Figure 10B:
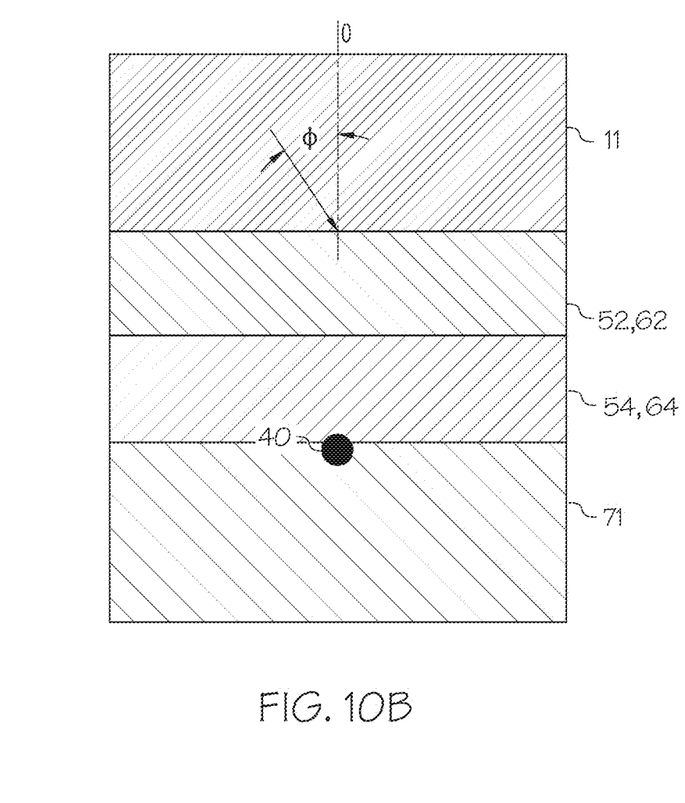
FIG. 10B depicts an acoustic body heartbeat monitoring configuration; according to one or more embodiments shown and described herein.

Turning now to FIGS. 8A-10B, illustrative examples of experimental results relating to transmission losses associated with different configurations for monitoring a heartbeat sound are depicted. The data presented in the charts is based on a 10 Hz acoustic signal impinging the microphone 40 at angle of incidences, $\phi$, from 0 degrees to 90 degrees. However, the most relevant angle of incidence, $\phi$, for applications described herein is 0 degrees to about 40 degrees. FIGS. 8A and 8B correspond to an air gaped configuration where the microphone 40 is positioned remotely from the body 11 with air being the medium between the body 11 and the microphone 40. As discussed above, transmission of sounds waves from a body 11 like material to air are very lossy. Here, at an angle of incidence, $\phi$, of 0 degrees only about −35 dB of the sound is transferred. Turning to FIGS. 9A and 9B the chart and diagram correspond to a body 11 to rigid plate 71 configuration. While the transmission of sound between a body 11 and a rigid plate 71 is an improvement over the air gaped configuration, with a −10 dB transmission near an angle of incidence, $\phi$, of 0 degrees, the rigid plate 71 configuration does not provide a workable option for integrating heartbeat sound monitoring into a seat, such as a vehicle seat, 20, for example. Turning to FIGS. 10A and 10B the chart and diagram correspond to acoustic body 50 and 60 implementations depicted and described herein. Acoustic bodies having two or more materials that can deliver very good transmission of sound near an angle of incidence, $\phi$, of 0 degrees. For example, at an angle of incidence, $\phi$, of about 0 degrees, there is transmission loss of less than −5 dB and more specifically about −1.5 dB.

Accordingly, it should be understood that embodiments described herein provide vastly improved systems for acoustically monitoring a heartbeat through a seat, such as a vehicle seat, and transferring the heartbeat sound to a microphone located remotely from the body as compared to an air gapped configuration and rigid plate configurations. More specifically, embodiments of the present disclosure include systems for acoustically monitoring a heartbeat having a first material in contact with a second material forming an acoustic body, a seat covering material in contact with a first surface of the acoustic body, and a microphone acoustically coupled to a second surface of the acoustic body. A density and a propagation speed of sound of the first material is matched with a density and a propagation speed of sound of a human body, and a density and a propagation speed of sound of the second material is matched with the density and the propagation speed of sound of the first material.

Further embodiments, include a system that includes a first material in contact with a second material forming an acoustic body, a seat covering material in contact with a first surface of the acoustic body, a dome shaped material coupled to the second surface of the acoustic body, and a microphone is positioned within the second material of the acoustic body and an acoustic sensitive element of the microphone is directionally positioned toward the dome shaped material. A density and a propagation speed of sound of the first material is matched with a density and a propagation speed of sound of a human body, a density and a propagation speed of sound of the second material is matched with the density and the propagation speed of sound of the first material, and the dome shaped material is significantly more or less dense than the density of the second material. In other words, the acoustic impedance of the dome shaped material is significantly different from the acoustic impedance of the second material resulting in a large reflection of sound from the interface between the dome shaped material and the second material.

Some applications include implementing the systems described herein within a seat, such as a vehicle seat. For example, a vehicle seat may include a first material in contact with a second material forming an acoustic body, where the acoustic body is positioned within the vehicle seat, a seat covering material of the vehicle seat in contact with a first surface of the acoustic body, and a microphone acoustically coupled to a second surface of the acoustic body. A density and a propagation speed of sound of the first material is matched with a density and a propagation speed of sound of a human body, and a density and a propagation speed of sound of the second material is matched with the density and the propagation speed of sound of the first material. However, it is understood that implementations are not limited to vehicle seats. Other implementations may include hospital beds, wheel chairs, couches, chairs, or other furniture.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A system for acoustically monitoring a heartbeat, the system comprising:
   an acoustic body having a first material in contact with a second material different from the first material, a density and a propagation speed of sound of the first material is matched with a density and a propagation speed of sound of a human body, and a density and a propagation speed of sound of the second material is matched with the density and the propagation speed of sound of the first material;
   a covering material in contact with a first surface of the acoustic body formed by the first material; and
   a microphone acoustically coupled to a second surface of the acoustic body formed by the second material.

2. The system of claim 1, wherein a transmission loss of an acoustic signal from the covering material to the microphone is less than −5 dB.

3. The system of claim 1, wherein the covering material is a seat covering of a seat.

4. The system of claim 1, further comprising a microphone mount configured to mount the microphone to the second side of the acoustic body, and
   wherein a density and a propagation speed of sound of the microphone mount is greater than the density and the propagation speed of sound of the second material.

5. The system of claim 1, wherein the acoustic body includes at least one additional material.

6. The system of claim 1, wherein an acoustic sensitive element of the microphone is directionally positioned toward the covering material.

7. The system of claim 1, wherein the density of the first material is between 1200 kg/m$^3$ and 1700 kg/m$^3$ and the propagation speed of sound of the first material is between 1500 m/s and 2000 m/s.

8. The system of claim 1, wherein the density of the second material is between 1500 kg/m$^3$ and 2500 kg/m$^3$ and the propagation speed of sound of the second material is between 1800 m/s and 3000 m/s.

9. The system of claim 1, wherein the first material is a liquid and the second material is a solid.

10. The system of claim 1, wherein the second material is a matrix material comprising a matrix having a fill factor that increases as a distance from the first surface of the acoustic body increases, and the matrix is filled with the first material.

11. The system of claim 10, wherein the first material is one of a liquid or a gel.

12. The system of claim 1, wherein an acoustic signal is transmitted through the first material and then through the second material toward the microphone.

13. The system of claim 1, further comprising a metamaterial structure positioned within or adjacent the acoustic body.

14. The system of claim 13, wherein the metamaterial structure is configured to filter out frequencies higher than 150 Hz.

15. A system for acoustically monitoring a heartbeat, the system comprising:
   an acoustic body having a first material in contact with a second material, a density and a propagation speed of sound of the first material is matched with a density and a propagation speed of sound of a human body, and a density and a propagation speed of sound of the second material is matched with the density and the propagation speed of sound of the first material;
   a covering material in contact with a first surface of the acoustic body;
   a dome shaped material coupled to a second surface of the acoustic body, the dome shaped material has an acoustic impedance that is greater or less than the acoustic impedance of the second material; and
   a microphone is positioned within the second material of the acoustic body and an acoustic sensitive element of the microphone is directionally positioned toward the dome shaped material.

16. The system of claim 15, wherein the dome shaped material is a metallic material.

17. The system of claim 15, wherein a transmission loss of an acoustic signal from the covering material to the microphone is less than −5 dB.

18. The system of claim 15, wherein an acoustic signal propagates through the first material and the second material, and a portion of the acoustic signal reflects off the dome shaped material toward the microphone.

19. A vehicle seat for a vehicle comprising:
   a first material in contact with a second material different from the first material, the second material forming an acoustic body, the acoustic body is positioned within the vehicle seat;
   a covering material of the vehicle seat in contact with a first surface of the acoustic body; and
   a microphone acoustically coupled to a second surface of the acoustic body, wherein a density and a propagation speed of sound of the first material is matched with a density and a propagation speed of sound of a human body, and a density and a propagation speed of sound of the second material is matched with the density and the propagation speed of sound of the first material.

20. The vehicle seat of claim 19, wherein transmission loss of an acoustic signal from the covering material to the microphone is less than −5 dB.

* * * * *

UNITED STATES PATENT AND TRADEMARK OFFICE
CERTIFICATE OF CORRECTION

| | |
|---|---|
| PATENT NO. | : 11,553,849 B2 |
| APPLICATION NO. | : 17/233985 |
| DATED | : January 17, 2023 |
| INVENTOR(S) | : Paul D. Schmalenberg, Ercan Mehmet Dede and Frederico Marcolino Quintao Severgnini |

It is certified that error appears in the above-identified patent and that said Letters Patent is hereby corrected as shown below:

In the Specification

In Column 2, Line(s) 53, delete "an", and insert --a--, therefor.

In Column 5, Line(s) 67, delete "db", and insert --dB--, therefor.

In Column 9, Line(s) 16, delete "Jandali", and insert --Jahdali--, therefor.

Signed and Sealed this
Fourteenth Day of March, 2023

Katherine Kelly Vidal
*Director of the United States Patent and Trademark Office*